(12) United States Patent
Saito et al.

(10) Patent No.: US 10,947,490 B2
(45) Date of Patent: Mar. 16, 2021

(54) LIQUID DELIVERY DEVICE AND CELL CULTURE DEVICE USING THE SAME

(71) Applicant: HITACHI, LTD., Tokyo (JP)

(72) Inventors: Hikaru Saito, Tokyo (JP); Masaharu Kiyama, Tokyo (JP); Midori Kato, Tokyo (JP); Kunio Ohyama, Tokyo (JP); Guangbin Zhou, Tokyo (JP); Hiroko Hanzawa, Tokyo (JP); Shizu Takeda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 441 days.

(21) Appl. No.: 15/896,947

(22) Filed: Feb. 14, 2018

(65) Prior Publication Data

US 2018/0362915 A1  Dec. 20, 2018

(30) Foreign Application Priority Data

Jun. 16, 2017  (JP) .............................. JP2017-118867

(51) Int. Cl.
*C12M 1/00* (2006.01)
*C12M 1/36* (2006.01)
(Continued)

(52) U.S. Cl.
CPC ............ *C12M 29/26* (2013.01); *C12M 21/08* (2013.01); *C12M 23/20* (2013.01); *C12M 25/14* (2013.01);
(Continued)

(58) Field of Classification Search
CPC .............................. C12M 21/08; C12M 29/00
See application file for complete search history.

(56) References Cited

U.S. PATENT DOCUMENTS

2006/0115889 A1   6/2006 Nakashima et al.
2010/0317102 A1*  12/2010 Suzuki ................... C12M 33/04
                                          435/366

FOREIGN PATENT DOCUMENTS

JP      2006149268 A    6/2006
JP      2007222120 A    9/2007
(Continued)

OTHER PUBLICATIONS

Notice of Reasons for Refusal for related Japanese Patent Application No. 2017-118867 dated Sep. 23, 2020; English translation provided (6 pages).

*Primary Examiner* — Jonathan M Hurst
(74) *Attorney, Agent, or Firm* — Procopio, Cory, Hargreaves & Savitch LLP (57) ABSTRACT

A liquid delivery device includes a first and second container for a first and second liquid; a third container for receiving a first and second liquid; a fourth container into which a first and second liquid are discharged; a fifth container for a third liquid; a first liquid delivery tube for delivering a first liquid; a second liquid delivery tube for delivering a second liquid; a third liquid delivery tube connected to the first and second liquid delivery tube; a first liquid delivery pump on the third liquid delivery tube; a fourth liquid delivery tube for discharging a first liquid contained in the third container and delivering a third liquid to the third container; a fifth liquid delivery tube connected to the fourth liquid delivery tube; a sixth liquid delivery tube connected to the fourth liquid delivery tube; and a second liquid delivery pump on the fourth liquid delivery tube.

9 Claims, 4 Drawing Sheets

(51) Int. Cl.
*C12M 1/34* (2006.01)
*C12M 1/12* (2006.01)
*C12M 3/00* (2006.01)

(52) U.S. Cl.
CPC ............ *C12M 29/00* (2013.01); *C12M 41/44* (2013.01); *C12M 41/48* (2013.01)

(56) References Cited

FOREIGN PATENT DOCUMENTS

| JP | 2012055227 A | 3/2012 |
| WO | 2007/083465 A1 | 7/2007 |
| WO | 2016/182978 A1 | 11/2016 |

\* cited by examiner

LIQUID DELIVERY DEVICE AND CELL CULTURE DEVICE USING THE SAME

CROSS REFERENCE TO RELATED DOCUMENTS

This application claims the benefit of Japanese Patent Application No. 2017-118867 filed on Jun. 16, 2017, the entire disclosure of which is hereby incorporated by reference.

TECHNICAL FIELD

The present invention relates to liquid delivery devices and cell culture devices using the same.

BACKGROUND ART

Cell culture devices that enable automated cell culture have been developed in recent years. The use of a cell culture device with a closed culture chamber, which does not require opening and closing of a lid of the culture chamber, can reduce the risk of biological contamination.

For some cells to be cultured, the culture chamber should be coated with a scaffold material before starting cell culture in order to improve adhesion of the cells to the culture chamber. In automated cell culture devices, a dispenser for a scaffold solution may be mechanized to cooperate with dispensing and transferring of the scaffold solution, thereby adding the scaffold material as in cases of manual operations (JP-A-2006-149268). Another method involves the use of a pump for dispensing a fixed volume of the scaffold solution, with a scaffold solution bottle and a culture dish being connected with each other using a disposable tube (JP-A-2007-222120; JP-A-2012-55227).

SUMMARY OF THE INVENTION

Problems to be Solved by the Invention

An object of the present invention is to provide novel liquid delivery devices and cell culture devices using the same.

Means to Solve the Problems

A first aspect of the present invention is a liquid delivery device including: a first container for a first liquid; a second container for a second liquid; a third container for receiving the first liquid and the second liquid; a fourth container into which a first liquid and a second liquid are discharged; a fifth container for a third liquid; a first liquid delivery tube for delivering a first liquid; a second liquid delivery tube for delivering a second liquid; a third liquid delivery tube connected to the first liquid delivery tube and the second liquid delivery tube, the third liquid delivery tube delivering to the third container first and second liquids that are present in the first and second liquid delivery tubes, respectively; a first liquid delivery pump provided on the third liquid delivery tube, the first liquid delivery pump controlling liquid delivery through the third liquid delivery tube; a fourth liquid delivery tube for discharging a first liquid contained in the third container and delivering a third liquid to the third container; a fifth liquid delivery tube connected to the fourth liquid delivery tube, the fifth liquid delivery tube delivering a third liquid contained in the fifth container to the third container through the fourth liquid delivery tube; a sixth liquid delivery tube connected to the fourth liquid delivery tube, the sixth liquid delivery tube discharging a first liquid contained in the third container into the fourth container through the fourth liquid delivery tube; and a second liquid delivery pump provided on the fourth liquid delivery tube, and the second liquid delivery pump controlling liquid delivery through the fourth liquid delivery tube. Each of the first, second, fifth, and sixth liquid delivery tubes may be provided with a valve.

Another aspect of the present invention is a liquid delivery device including: a first container for a cell culture medium; a second container for a cell suspension; a third container for culturing cells; a fourth container into which a liquid waste after cell culture is discarded; a fifth container for a scaffold solution containing a cell scaffold material; a first liquid delivery tube for delivering a cell culture medium contained in the first container; a second liquid delivery tube for delivering a cell suspension contained in the second container; a third liquid delivery tube connected to the first liquid delivery tube and the second liquid delivery tube, the third liquid delivery tube delivering to the third container a cell culture medium and a cell suspension that are present in the first liquid delivery tube and the second liquid delivery tube, respectively; a first liquid delivery pump provided on the third liquid delivery tube, the first liquid delivery pump controlling liquid delivery through the third liquid delivery tube; a fourth liquid delivery tube for discharging a cell culture medium contained in the third container and delivering a scaffold solution to the third container; a fifth liquid delivery tube connected to the fourth liquid delivery tube, the fifth liquid delivery tube delivering a scaffold solution contained in the fifth container to the third container through the fourth liquid delivery tube; a sixth liquid delivery tube connected to the fourth liquid delivery tube, the sixth liquid delivery tube discharging a cell culture medium contained in the third container into the fourth container through the fourth liquid delivery tube; and a second liquid delivery pump provided on the fourth liquid delivery tube, the second liquid delivery pump controlling liquid delivery through the fourth liquid delivery tube. Each of the first, second, fifth, and sixth liquid delivery tubes may be provided with a valve. The cells may be stem cells. The cell scaffold material may include fibronectin, collagen, albumin, laminin, polylysine, polyornithine, or gelatin.

A yet another aspect of the present invention is a cell culture device having any one or more of the aforementioned liquid delivery devices.

INDUSTRIAL APPLICABILITY

The present invention made it possible to provide novel liquid delivery devices and cell culture devices using the same.

DETAILED DESCRIPTION OF THE EMBODIMENTS

Hereinafter, various embodiments of the present invention are described with reference to the accompanying drawings. These embodiments are, however, merely examples for achieving the present invention, and do not limit the technical scope of the present invention. It is to be noted that the same reference numerals are given to the same components in the figures.

<Liquid Delivery Device I>

An exemplified configuration of a liquid delivery device I is described below.

Figure 1:
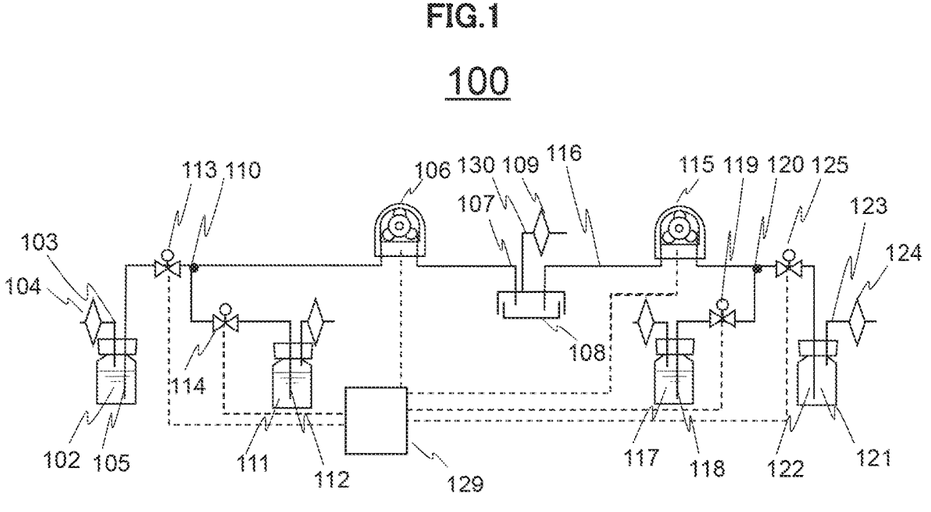
FIG. 1 is a configuration diagram of a liquid delivery device I according to an embodiment of the present invention.

A liquid delivery device 100 has a first container 102 containing a first liquid, a second container 111 containing a second liquid, and a third container 108 containing the first and second liquids.

The first container 102, the second container 111, and the third container 108 can be produced easily in view of their purposes according to the common technical knowledge of those skilled in the art. Each of the containers has its own air pressure adjustment tube 103 that is open to the atmospheric air and has an end located in the gas phase in the container. The third container 108 can also be produced easily in view of its purpose according to the common technical knowledge of those skilled in the art. The third container 108 has an air pressure adjustment tube 130 that is open to the atmospheric air and has an end located in the gas phase in the container.

The liquid delivery device 100 has a first liquid delivery tube 105 for delivering the first liquid contained in the first container 102, a second liquid delivery tube 112 for delivering the second liquid contained in the second container 111, and a third liquid delivery tube 107 that is connected to the first liquid delivery tube 105 and the second liquid delivery tube 112 for delivering, to the third container 108, the first liquid in the first liquid delivery tube 105 and the second liquid in the second liquid delivery tube 112. The third liquid delivery tube 107 has a first liquid delivery pump 106 that controls the delivery of the liquid through the third liquid delivery tube 107. Each of the liquid delivery tubes can be produced easily according to the common technical knowledge of those skilled in the art. For example, the first liquid delivery tube 105 and the third liquid delivery tube 107 may be provided as a single tube and connected to the second liquid delivery tube 112. Likewise, the second liquid delivery tube 112 and the third liquid delivery tube 107 may be provided as a single tube and connected to the first liquid delivery tube 105. The first liquid delivery tube 105 and the second liquid delivery tube 112 have a first valve 113 and a second valve 114, respectively, with which the delivery and non-delivery of the liquid through the tubes can be controlled by opening and closing them.

The liquid delivery device 100 has a fourth container 121 into which the first liquid in the third container 108 is discarded and a fifth container 117 containing a third solution. The fourth container 121 and the fifth container 117 can be produced easily according to the common technical knowledge of those skilled in the art in view of their purposes. Each of the containers has an air pressure adjustment tube 123 that is open to the atmospheric air and has an end located in the gas phase in the container. It is preferable that the third solution is viscous. Being viscous, the third solution does not foul the first, second, and third liquid delivery tubes.

The liquid delivery device 100 also has a fourth liquid delivery tube 116 for discharging the first liquid contained in the third container 108 and delivering the third solution to the third container 108, a fifth liquid delivery tube 118 that is connected to the fourth liquid delivery tube 116 and delivers the third solution contained in the fifth container 117 to the third container 108 via the fourth liquid delivery tube 116, and a sixth liquid delivery tube 122 that is connected to the fourth liquid delivery tube 116 and discharges the first liquid contained in the third container 108 to the fourth container 121 via the fourth liquid delivery tube 116. The fourth liquid delivery tube 116 has a second liquid delivery pump 115 that controls the liquid delivery through the fourth liquid delivery tube 116. Each liquid delivery tube can be produced easily according to the common technical knowledge of those skilled in the art. For example, the fourth liquid delivery tube 116 and the fifth liquid delivery tube 118 may be provided as a single tube and connected to the sixth liquid delivery tube 122 at a junction 120 or the fourth liquid delivery tube 116 and the sixth liquid delivery tube 122 may be provided as a single tube and connected to the fifth liquid delivery tube 118 at the junction 120. The fifth liquid delivery tube 118 and the sixth liquid delivery tube 122 have a third valve 119 and a fourth valve 125, respectively, with which the delivery and non-delivery of the liquid through the tubes can be controlled by opening and closing them.

It is preferable that a control unit 129 is provided so that the activation of the pumps and opening/closing of the valves may be automatically controlled.

As can be seen from the above, by separating the first to third liquid delivery tubes from the fourth and fifth liquid delivery tubes, none of the first, second, and third liquid delivery tubes is fouled with the third solution that is necessary for the third container 108. Furthermore, since the third solution is delivered using the pump that is used for discarding the first liquid, the configuration of the device can be simplified.

<Liquid Delivery Device II>

An exemplified case where the liquid delivery device is used for cell culture is described in detail below with reference to the liquid delivery device shown in FIG. 2.

A liquid delivery device 200 has a culture medium container 202 containing a cell culture medium, a cell container 211 containing a cell suspension, and a culture chamber 208 for culturing cells.

The culture medium container 202 and the cell container 211 can be produced easily according to the common technical knowledge of those skilled in the art. Each of them has an air pressure adjustment tube 203 that is open to the atmospheric air and has an end located in the gas phase in the container. The air pressure adjustment tube 203 has a filter 204 for sterilizing the atmospheric air flowing into the culture medium container 202 and the cell container 211. Accordingly, the filter 204 may be, for example, a sterilization filter with a 0.22 µm pore size. The cell culture medium can be appropriately selected by a person skilled in the art as long as it is suitable for the cells to be cultured. The cell suspension is a liquid obtained by suspending cells for culture in a culture medium or a buffer such as PBS at an appropriate concentration.

The culture chamber 208 is not specifically limited, but is preferably a culture dish or a culture bottle. It is preferable that the culture chamber 208 has a bottom without coating and may be, for example, a commercially available plastic dish for bacterial culture. The culture chamber 208 has an air pressure adjustment tube 230 that is open to the air and has an end located in the gas phase in the container. The air pressure adjustment tube 230 has a filter 209 for sterilizing the atmospheric air flowing into the culture chamber 208. Accordingly, the filter 209 may be, for example, a sterilization filter with a 0.22 μm pore size.

The liquid delivery device 200 has a culture medium delivery tube 205 for delivering a cell culture medium contained in the culture medium container 202, a cell suspension delivery tube 212 for delivering a cell suspension contained in the cell container 211, and a cultured cell delivery tube 207 that is connected to the culture medium delivery tube 5 and the cell suspension delivery tube 212 at a junction 210 and delivers to the culture chamber 208 the cell culture medium that is present in the culture medium delivery tube 205 and the cell suspension that is present in the cell suspension delivery tube 212. The cultured cell delivery tube 207 has a first liquid delivery pump 206 that controls the delivery of the liquid through the cultured cell delivery tube 207. Each of the liquid delivery tubes can be produced easily according to the common technical knowledge of those skilled in the art. For example, the culture medium delivery tube 205 and the cultured cell delivery tube 207 may be provided as a single tube and connected to the cell suspension delivery tube 212 at the junction 210. Likewise, the cell suspension delivery tube 212 and the cultured cell delivery tube 207 may be provided as a single tube and connected to the culture medium delivery tube 205 at the junction 210. The culture medium delivery tube 205 and the cell suspension delivery tube 212 have a culture medium delivery valve 213 and a cell suspension delivery valve 214, respectively, with which the delivery and non-delivery of the liquid through the tubes can be controlled by opening and closing them.

The liquid delivery device 200 also has two gas inlet tubes 231 and 241 that are communicated with the atmospheric air. The gas inlet tube 231 is connected to the cultured cell delivery tube 207 at a junction 226 and the gas inlet tube 241 is connected to a bi-directional liquid delivery tube 216 at a junction 236. The gas inlet tubes 231 and 241 have filters 227 and 237 for sterilizing the atmospheric air flowing into the liquid delivery device 200. Accordingly, the filters 227 and 237 may be sterilization filters having a mesh size of 0.22 μm. The gas inlet tubes 231 and 241 also have atmospheric air inflow valves 228 and 238 to start and stop the inflow of the atmospheric air. These gas inlet tubes 231 and 241 are used, when each of a plurality of culture chambers 208 is supplied with a culture medium from the culture medium container 202 or a scaffold material from a scaffold solution container 217, to open the atmospheric air inflow valves 228 and 238 and remove the culture medium present in the cultured cell delivery tube 207 or the scaffold material present in the bi-directional liquid delivery tube 216, before replacement of the culture chamber 208.

The liquid delivery device 200 also has a liquid waste container 221 into which a liquid waste after cell culture is discarded and the scaffold solution container 217 containing a scaffold solution with a cell scaffold material. The liquid waste container 221 and the scaffold solution container 217 can be produced easily according to the common technical knowledge of those skilled in the art. Each of the containers has an air pressure adjustment tube 223 that is open to the atmospheric air and has an end located in the gas phase in the container. The air pressure adjustment tube 223 has a filter 224 for sterilizing the atmospheric air flowing into the liquid waste container 221 and the scaffold solution container 217. Accordingly, the filter 224 may be, for example, a sterilization filter with a 0.22 μm pore size. The scaffold material is used for coating the bottom surface of the culture chamber 208 and promoting adhesion of the cells to be cultured and those suitable for the cells to be cultured can be chosen. For example, it may contain fibronectin, collagen, albumin, laminin, polylysine, polyornithine, or gelatin.

The liquid delivery device 200 also has a bi-directional liquid delivery tube 216 for discharging the cell culture medium contained in the culture chamber 208 and delivering the scaffold solution to the culture chamber 208, a scaffold solution delivery tube 218 that is connected to the bi-directional liquid delivery tube 216 and delivers the scaffold solution contained in the scaffold solution container 217 to the culture chamber 208 via the bi-directional liquid delivery tube 216, and a liquid waste delivery tube 222 that is connected to the bi-directional liquid delivery tube 216 and discharges the cell culture medium contained in the culture chamber 208 into the liquid waste container 221 via the bi-directional liquid delivery tube 216. The bi-directional liquid delivery tube 216 has a second liquid delivery pump 215 that controls the liquid delivery through the bi-directional liquid delivery tube 216. Each of the liquid delivery tubes can be produced easily according to the common technical knowledge of those skilled in the art. For example, the bi-directional liquid delivery tube 216 and the scaffold solution delivery tube 218 may be provided as a single tube and connected to the liquid waste delivery tube 222 at a junction 220. Likewise, the bi-directional liquid delivery tube 216 and the liquid waste delivery tube 222 may be provided as a single tube and connected to the scaffold solution delivery tube 218 at the junction 220. The scaffold solution delivery tube 218 and the liquid waste delivery tube 222 have a scaffold solution delivery valve 219 and a liquid waste delivery valve 225, respectively. By opening and closing the valves, the delivery and non-delivery of the liquid through the tubes can be controlled.

It is preferable that the containers, chambers and the liquid delivery tubes have tightly sealed structures. Such structures can keep their insides aseptic. It is also preferable that a control unit 229 is provided to allow automatic control of the activation of the pumps and opening/closing of the valves.

As can be seen from the above, by separating the scaffold solution delivery tube 218 from the cell suspension delivery tube 212, the cell suspension never flows through the tube through which the scaffold solution has already passed during the liquid delivery operation. This eliminates any chance for the cells in the cell suspension to be trapped at an improper place due to the scaffold solution left in the tube. Furthermore, since the scaffold solution is delivered using the pump that is used for delivering the liquid waste, the entire configuration of the device can be simplified.

<Method of Operating the Liquid Delivery Device>

Figure 3:
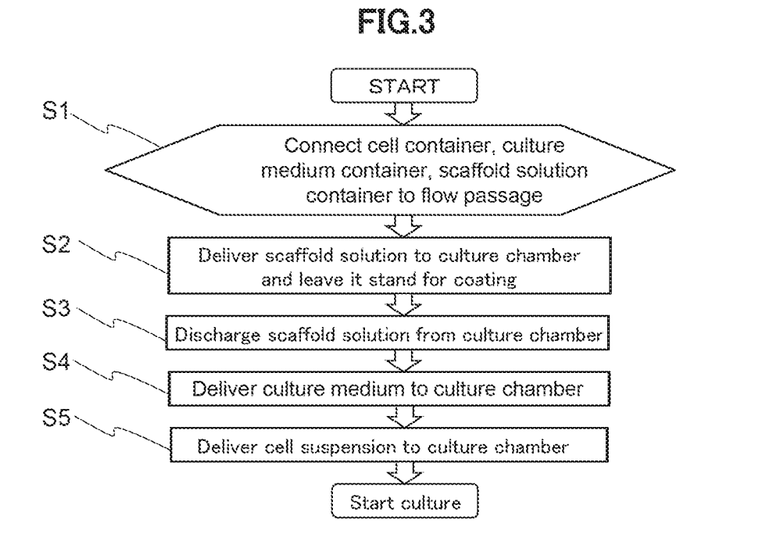
FIG. 3 shows a control flow of an automated cell culture device according to an embodiment of the present invention.
Figure 4:
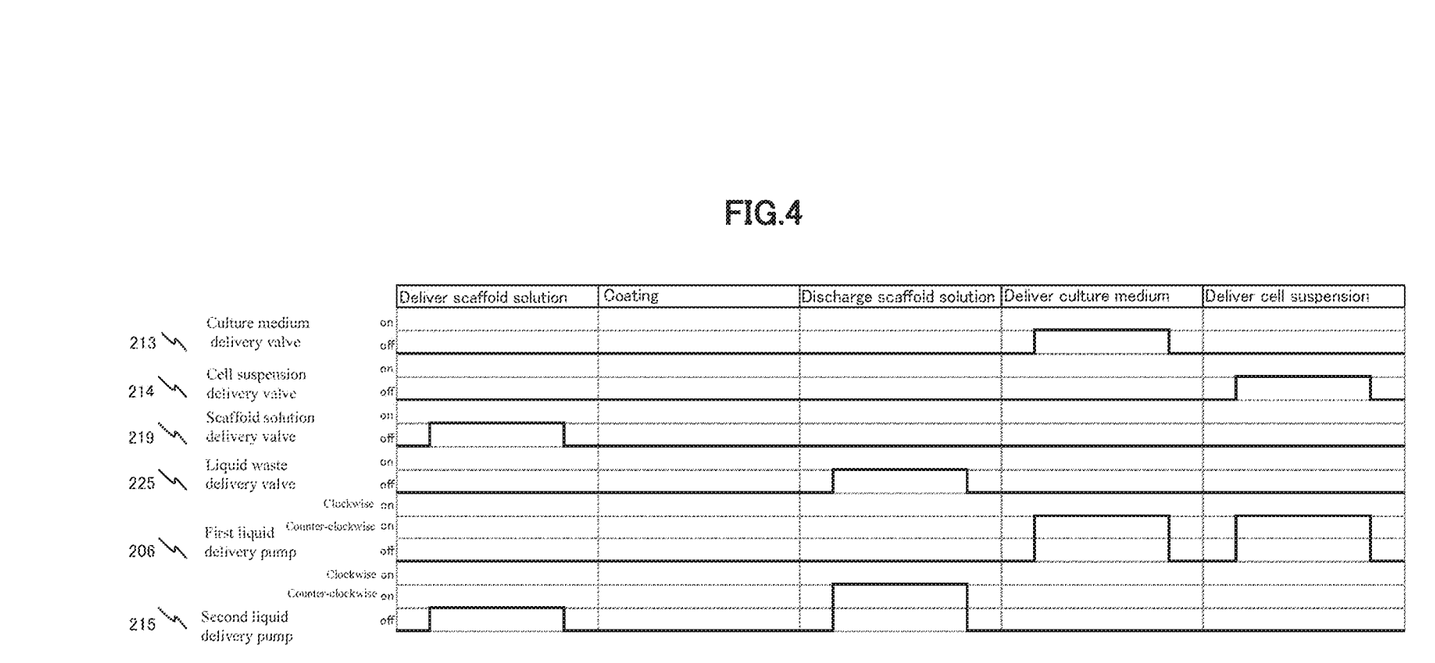
FIG. 4 is a control timing chart of a liquid delivery device according to an embodiment of the present invention.

Hereinafter, a method of operating the liquid delivery device 200 is described in detail using the liquid delivery device II as an example. The liquid delivery device 200 may be controlled manually or using the control unit 229. FIG. 3 shows a flow chart that is applied when the control is made by the control unit 229. Furthermore, FIG. 4 shows a method of controlling, with time, on (open) and off (close) of each liquid delivery valve and on and off of each liquid delivery pump. They are all in the off state at the beginning of the operation of the liquid delivery device.

(Step 1) Cells to be cultured are prepared in the cell container 211. A culture medium is prepared in the culture medium container 202. A scaffold solution is prepared in the scaffold solution container 217. The cell container 211, the culture medium container 202, the scaffold solution container 217, and the liquid waste container 221 are attached to the flow passage so that the configuration as shown in FIG. 1 is achieved (FIG. 3; S1).

(Step 2) The scaffold solution in the scaffold solution container 217 is delivered to the culture chamber 208 and the culture chamber 208 is coated with the solution (FIG. 3; S2). Details are specifically described below.

Figure 2:
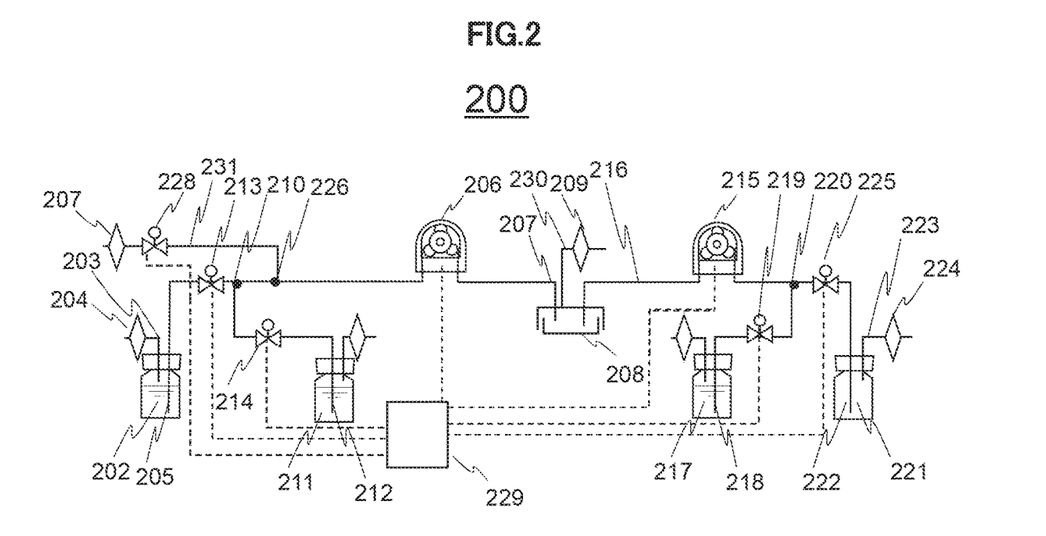
FIG. 2 is a configuration diagram of a liquid delivery device II according to an embodiment of the present invention.

When the second liquid delivery pump 215 is operated in the counter-clockwise direction in FIG. 2 after the liquid waste delivery valve 225 is closed and the scaffold solution delivery valve 219 is opened, the scaffold solution in the scaffold solution container 217 is delivered to the culture chamber 208 through the scaffold solution delivery tube 218 and the bi-directional liquid delivery tube 216. When the scaffold solution delivered from the scaffold solution delivery tube 218 to the culture chamber 208 reaches a predetermined volume, the second liquid delivery pump 215 is stopped and the culture chamber 208 is left stand for a predetermined time. Although the spatial volume in the scaffold solution container 217 is increased by the volume equal to that of the scaffold solution that has been delivered, the pressure in the scaffold solution container 217 is kept at atmospheric pressure because an equal amount of air is taken from the outside through the filter 227. If the culture chamber 208 is air-tight, the spatial volume in the culture chamber 208 is reduced by the volume equal to that of the scaffold solution that has been delivered. However, the pressure in the culture chamber 208 is kept at atmospheric pressure because an equal amount of air is discharged to the outside through the filter 209. The time for leaving it stand is not specifically limited and an appropriate time in a range of from 10 minutes to several hours can be selected from the standpoint of the technical knowledge.

(Step 3) The scaffold solution in the culture chamber 208 is discharged (FIG. 3; S3). Details are specifically described below.

When the second liquid delivery pump 215 is rotated in the clockwise direction in FIG. 2 after the scaffold solution delivery valve 219 is closed and the liquid waste delivery valve 225 is opened, the scaffold solution in the culture chamber 208 is discharged into the liquid waste container 221 through the bi-directional liquid delivery tube 216 and the liquid waste delivery tube 222. When the scaffold solution in the culture chamber 208 has been discharged almost completely, the second liquid delivery pump 215 is stopped and the liquid waste delivery valve 225 is closed. Although the spatial volume in the liquid waste container 221 is reduced by the volume equal to that of the scaffold solution that has been delivered, the pressure in the liquid waste container 221 is kept at atmospheric pressure because an equal amount of air is discharged to the outside through the filter 224. If the culture chamber 208 is air-tight, the spatial volume in the culture chamber 208 is increased by the volume equal to that of the scaffold solution that has been delivered. However, the pressure in the culture chamber 208 is kept at atmospheric pressure because an equal amount of air is taken from the outside through the filter 209.

(Step 4) The culture medium in the culture medium container 202 is delivered to the culture chamber 208 (FIG. 3; S4). Details are specifically described below.

When the cell suspension delivery valve 214 and the atmospheric air inflow valve 228 are closed and the culture medium delivery valve 213 is opened and then the first liquid delivery pump 206 is rotated in the clockwise direction in FIG. 2, the first liquid delivery pump 206 delivers the culture medium to the culture chamber 208 through the culture medium delivery tube 205 and the cultured cell delivery tube 207. When the culture medium delivered from the culture medium container 202 to the culture chamber 208 reaches a predetermined volume, the first liquid delivery pump 206 is stopped. Although the spatial volume in the culture medium container 202 is increased by the volume equal to that of the culture medium that has been delivered, the pressure in the culture medium container 202 is kept at atmospheric pressure because an equal amount of air is taken from the outside through the filter 204. If the culture chamber 208 is air-tight, the spatial volume in the culture chamber 208 is reduced by the volume equal to that of the culture medium that has been delivered. However, the pressure in the culture chamber 208 is kept at atmospheric pressure because an equal amount of air is discharged to the outside through the filter 209. Finally, when the atmospheric air inflow valve 228 is opened, the pressure in the entire device is adjusted finely to substantially atmospheric pressure.

At this point of time, one or more washing steps may be performed to wash off the scaffold solution that has not been able to be removed from the culture chamber 208 at step 203. In such a case, when the scaffold solution delivery valve 219 is closed and the liquid waste delivery valve 225 is opened and then the second liquid delivery pump 215 is rotated in the clockwise direction in FIG. 1, the culture medium in the culture chamber 208 is discharged into the liquid waste container 221 through the bi-directional liquid delivery tube 216 and the liquid waste delivery tube 222. When the scaffold solution in the culture chamber 208 has been discharged almost completely, the second liquid delivery pump 215 is stopped and the liquid waste delivery valve 225 is closed. Although the spatial volume in the liquid waste container 221 is reduced by the volume equal to that of the culture medium that has been delivered, the pressure in the liquid waste container 221 is kept at atmospheric pressure because an equal amount of air is discharged to the outside through the filter 224. If the culture chamber 208 is air-tight, the spatial volume in the culture chamber 208 is increased by the volume equal to that of the culture medium that has been delivered. However, the pressure in the culture chamber 208 is kept at atmospheric pressure because an equal amount of air is taken from the outside through the filter 209. Thereafter, as described above, the culture medium in the culture medium container 202 is again delivered to the culture chamber 208. If two or more washing steps are performed, this substep is repeated.

(Step 5) The cell suspension in the cell container 211 is delivered to the culture chamber 208 (FIG. 3; S5). Details are specifically described below.

When the culture medium delivery valve 213 and the atmospheric air inflow valve 228 are closed and the cell suspension delivery valve 214 is opened and then the first liquid delivery pump 206 is operated in the clockwise direction in FIG. 2, the first liquid delivery pump 206 delivers the cell suspension to the culture chamber 208 through the cell suspension delivery tube 212 and the cultured cell delivery tube 207. When the cell suspension delivered from the cell container 211 reaches a predetermined volume, the first liquid delivery pump 206 is stopped. Although the spatial volume in the cell container 211 is increased by the volume equal to that of the cell suspension that has been delivered, the pressure in the cell container 211 is kept at atmospheric pressure because an equal amount of air is taken from the outside through the filter 204. If the culture chamber 208 is air-tight, the spatial volume in the culture chamber 208 is reduced by the volume equal to that of the cell suspension that has been delivered. However, the pressure in the culture chamber 208 is kept at atmospheric pressure because an equal amount of air is discharged to the outside through the filter 209. Finally, when the atmospheric air inflow valve 228 is opened, the pressure in the entire device is adjusted finely to the exact atmospheric pressure.

DENOTATION OF SYMBOLS

100 . . . liquid delivery device, 102 . . . first container, 103 . . . air pressure adjustment tube, 104 . . . filter, 105 . . . first liquid delivery tube, 106 . . . first liquid delivery pump, 107 . . . third liquid delivery tube, 108 . . . third container, 109 . . . filter, 110 . . . junction, 111 . . . second container, 112 . . . second liquid delivery tube, 113 . . . first valve, 114 . . . second valve, 115 . . . second liquid delivery pump, 116 . . . fourth liquid delivery tube, 117 . . . fifth container, 118 . . . fifth liquid delivery tube, 119 . . . third valve, 120 . . . junction, 121 . . . fourth container, 122 . . . sixth liquid delivery tube, 123 . . . air pressure adjustment tube, 124 . . . filter, 125 . . . fourth valve, 129 . . . control unit, 130 . . . air pressure adjustment tube, 201 . . . liquid delivery device, 202 . . . culture medium container, 203 . . . air pressure adjustment tube, 204 . . . filter, 205 . . . culture medium delivery tube 5, 206 . . . first liquid delivery pump, 207 . . . cultured cell delivery tube, 208 . . . culture chamber, 209 . . . filter, 210 . . . junction, 211 . . . cell container, 212 . . . cell suspension delivery tube, 213 . . . culture medium delivery valve, 214 . . . cell suspension delivery valve, 215 . . . second liquid delivery pump, 216 . . . bi-directional liquid delivery tube, 217 . . . scaffold solution container, 218 . . . scaffold solution delivery tube, 219 . . . scaffold solution delivery valve, 220 . . . junction, 221 . . . liquid waste container, 222 . . . liquid waste delivery tube, 223 . . . air pressure adjustment tube, 224 . . . filter, 225 . . . liquid waste delivery valve, 226 . . . junction, 227 . . . filter, 228 . . . atmospheric air inflow valve, 229 . . . control unit, 230 . . . air pressure adjustment tube, 231 . . . atmospheric air inflow tube, 236 . . . junction, 237 . . . filter, 238 . . . atmospheric air inflow valve, 241 . . . atmospheric air inflow tube

The invention claimed is:

1. A liquid delivery device comprising:
a first container for a first liquid;
a second container for a second liquid;
a third container for receiving the first liquid and the second liquid;
a fourth container into which the first liquid and the second liquid are discharged;
a fifth container for a third liquid;
a first liquid delivery tube for delivering the first liquid;
a second liquid delivery tube for delivering the second liquid;
a third liquid delivery tube connected to the first liquid delivery tube and the second liquid delivery tube, the third liquid delivery tube delivering to the third container first and second liquids that are present in the first and second liquid delivery tubes, respectively;
a first liquid delivery pump provided on the third liquid delivery tube, the first liquid delivery pump controlling liquid delivery through the third liquid delivery tube;
a bi-directional fourth liquid delivery tube for discharging the first liquid contained in the third container and delivering the third liquid to the third container;
a fifth liquid delivery tube connected to the bi-directional fourth liquid delivery tube, the fifth liquid delivery tube delivering a third liquid contained in the fifth container to the third container through the bi-directional fourth liquid delivery tube;
a sixth liquid delivery tube connected to the bi-directional fourth liquid delivery tube, the sixth liquid delivery tube discharging the first liquid contained in the third container into the fourth container through the bi-directional fourth liquid delivery tube;
a second liquid delivery pump provided on the bi-directional fourth liquid delivery tube, the second liquid delivery pump controlling liquid delivery of the third liquid from the fifth container into the third container, and the first liquid from the third container into the fourth container through the bi-directional fourth liquid delivery tube; and
a controller coupled to the first liquid delivery pump and the second liquid delivery pump, the controller configured to operate the first and second liquid delivery pumps to:
control the first liquid delivery pump to operate in a first direction and deliver the first and second liquids that are present in the first liquid delivery tube and the second liquid delivery tube, respectively, through the third liquid delivery tube to the third container,
control the second liquid delivery pump to operate in a second direction and deliver the third solution contained in the fifth container to the third container via the bi-directional fourth liquid delivery tube, and
control the second liquid delivery pump to operate in a third direction opposite the second direction and deliver the first liquid from the third container into the fourth container through the bi-directional fourth liquid delivery tube.

2. The liquid delivery device according to claim 1, wherein each of the first, second, fifth, and sixth liquid delivery tubes is provided with a valve.

3. A liquid delivery device comprising:
a first container for a cell culture medium;
a second container for a cell suspension;
a third container for culturing cells;
a fourth container into which a liquid waste after cell culture is discarded;
a fifth container for a scaffold solution containing a cell scaffold material;
a first liquid delivery tube for delivering the cell culture medium contained in the first container;
a second liquid delivery tube for delivering the cell suspension contained in the second container;
a third liquid delivery tube connected to the first liquid delivery tube and the second liquid delivery tube, the third liquid delivery tube delivering to the third container the cell culture medium and the cell suspension that are present in the first liquid delivery tube and the second liquid delivery tube, respectively;
a first liquid delivery pump provided on the third liquid delivery tube, the first liquid delivery pump controlling liquid delivery through the third liquid delivery tube;
a bi-directional fourth liquid delivery tube for discharging the cell culture medium contained in the third container and delivering the scaffold solution to the third container;
a fifth liquid delivery tube connected to the bi-directional fourth liquid delivery tube, the fifth liquid delivery tube delivering the scaffold solution contained in the fifth container to the third container through the bi-directional fourth liquid delivery tube;
a sixth liquid delivery tube connected to the bi-directional fourth liquid delivery tube, the sixth liquid delivery tube discharging the cell culture medium contained in the third container into the fourth container through the bi-directional fourth liquid delivery tube;
a second liquid delivery pump provided on the bi-directional fourth liquid delivery tube, the second liquid delivery pump controlling liquid delivery of the scaffold solution contained in the fifth container to the third container, and the cell culture medium from the third container into the fourth container through the bi-directional fourth liquid delivery tube; and
a controller coupled to the first liquid delivery pump and the second liquid delivery pump, the controller configured to operate the first and second liquid delivery pumps to:
control the first liquid delivery pump to operate in a first direction and deliver the cell culture medium and the cell suspension that are present in the first liquid delivery tube and the second liquid delivery tube, respectively, through the third liquid delivery tube to the third container,
control the second liquid delivery pump to operate in a second direction and deliver the scaffold solution contained in the fifth container to the third container via the bi-directional fourth liquid delivery tube, and
control the second liquid delivery pump to operate in a third direction opposite the second direction and deliver the cell culture medium from the third container into the fourth container through the bi-directional fourth liquid delivery tube.

4. The liquid delivery device according to claim 3, wherein each of the first, second, fifth, and sixth liquid delivery tubes is provided with a valve.

5. The liquid delivery device according to claim 3, wherein the cells are stem cells.

6. The liquid delivery device according to claim 3, wherein the cell scaffold material comprises fibronectin, collagen, albumin, laminin, polylysine, polyornithine, or gelatin.

7. A cell culture device comprising one or more of the liquid delivery devices according to claim 3.

8. The liquid delivery device according to claim 3, wherein the controller is further configured to:
control the second liquid delivery pump to operate in the second direction and deliver the scaffold solution contained in the fifth container to the third container via the bi-directional fourth liquid delivery tube until the scaffold solution reaches a first predetermined volume in the third container,
after a predetermined time period following reaching the first predetermined volume, control the second liquid delivery pump to operate in the third direction and deliver the scaffold solution from the third container into the fourth container through the bi-directional fourth liquid delivery tube,
after the scaffold solution is delivered to the fourth container, control the first liquid delivery pump to operate in the first direction and deliver the cell culture medium present in the first liquid delivery tube through the third liquid delivery tube to the third container until the cell culture medium reaches a second predetermined volume, and
after the cell culture medium reaches the second predetermined volume in the third container, control the first liquid delivery pump to operate in the first direction and deliver the cell suspension present in the second liquid delivery tube through the third liquid delivery tube to the third container until the cell suspension medium reaches a third predetermined volume.

9. The liquid delivery device according to claim 8, wherein the controller is further configured to:
after the cell culture medium reaches the second predetermined volume in the third container and before delivery of the cell suspension to the third container, control the second liquid delivery pump to operate in the third direction and deliver the cell culture medium from the third container into the fourth container through the bi-directional fourth liquid delivery tube.

* * * * *